United States Patent
Leftheris et al.

[11] Patent Number: 6,156,746
[45] Date of Patent: Dec. 5, 2000

[54] 1,2,5-BENZOTHIADIAZEPINE-1,1-DIOXIDES WITH N-2 IMIDAZOLYLALKYL SUBSTITUENTS

[75] Inventors: Katerina Leftheris, Skillman; John T. Hunt, Princeton; Charles Z. Ding, Plainsboro, all of N.J.

[73] Assignee: Bristol-Myers Squibb Company, Princeton, N.J.

[21] Appl. No.: 09/354,038

[22] Filed: Jul. 15, 1999

Related U.S. Application Data

[60] Provisional application No. 60/097,924, Aug. 25, 1998, and provisional application No. 60/106,625, Nov. 2, 1998.

[51] Int. Cl.[7] ............ A61K 31/551; C07D 419/14; C07D 417/06
[52] U.S. Cl. .............. 514/211.06; 540/489; 540/542; 540/545; 514/211.07; 514/211.08
[58] Field of Search .................... 540/542, 489, 540/545; 514/211.06, 211.07, 211.08

[56] References Cited

FOREIGN PATENT DOCUMENTS

WO 98/02436  1/1998  WIPO .

Primary Examiner—Joseph McKane
Assistant Examiner—Sonya N Wright
Attorney, Agent, or Firm—Timothy J. Babcock

[57] ABSTRACT

Inhibition of farnesyl transferase, which is an enzyme involved in ras oncogene expression, is effected by compounds of the formula

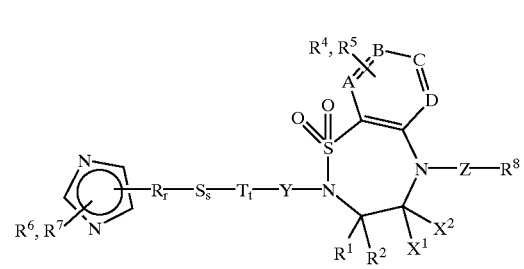

and their enantiomers, diastereomers, and their pharmaceutically acceptable salts, including prodrugs and solvates thereof.

The compounds of formula I are useful in the treatment of a variety of cancers. In addition, the formula I compounds may also be useful in the treatment of diseases other than cancer.

9 Claims, No Drawings

1,2,5-BENZOTHIADIAZEPINE-1,1-DIOXIDES WITH N-2 IMIDAZOLYLALKYL SUBSTITUENTS

This application claims the benefit of U.S. Provisional Application No. 60/097,924 filed Aug. 25, 1998 and U.S. Provisional Application No. 60/106,625 filed Nov. 2, 1998.

FIELD OF THE INVENTION

This invention relates to compounds that inhibit farnesyl protein transferase and ras protein farnesylation, thereby making them useful as anti-cancer agents. The compounds are also useful in the treatment of diseases, other than cancer, associated with signal transduction pathways operating through ras and those associated with CAAX-containing proteins other than ras that are also post-translationally modified by the enzyme farnesyl protein transferase. The compounds may also act as inhibitors of other prenyl transferases, and thus be effective in the treatment of diseases associated with other prenyl modifications of proteins.

BACKGROUND OF THE INVENTION

The mammalian ras gene family comprises three genes, H-ras, K-ras and N-ras. The ras proteins are a family of GTP-binding and hydrolyzing proteins that regulate cell growth and differentiation. Overproduction of normal ras proteins or mutations that inhibit their GTPase activity can lead to uncontrolled cell division. The transforming activity of ras is dependent on localization of the protein to plasma membranes. This membrane binding occurs via a series of posttranslational modifications of the cytosolic ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The ras C-terminus contains a sequence motif termed a "Cys-Aaa1-Aaa2-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thio-ether linkage.

BRIEF DESCRIPTION OF THE INVENTION

In accordance with the present invention, compounds of the formula

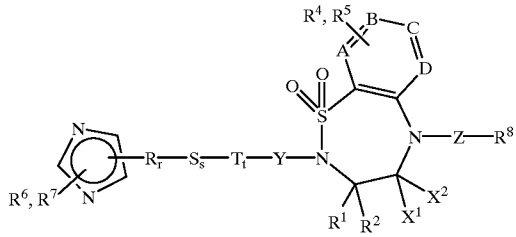

(I)

their enantiomers, diastereomers, and pharmaceutically acceptable salts, prodrugs and solvates thereof inhibit farnesyl protein transferase which is an enzyme involved in ras oncogene expression. In formula I and throughout the specification, the above symbols are defined as follows:

r, s and t are 0 or 1;

p is 0, 1, or 2;

$X^1$ and $X^2$ are each independently selected from the group consisting of hydrogen, alkyl, substituted alkyl, akenyl, substituted alkenyl, alkynyl, substituted alkynyl, aralkyl, cycloalkyl, aryl, substituted aryl, heterocyclo, substituted heterocyclo or when $X^1$ and $X^2$ are taken together they represent an oxygen atom double bonded to the carbon atom of the ring;

Y is selected from the group consisting of $CHR^9$, $CR^9R^{10}$;

Z is —CO—, —$SO_2$— or Z is absent;

$R^6$, $R^7$, $R^9$, $R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$, are selected from the group consisting of hydrogen, lower alkyl or substituted alkyl;

$R^4$, $R^5$ are selected from the group consisting of hydrogen, halo, nitro, cyano and U—$R^{11}$; $R^4$ and $R^5$ may join together to form a carbocyclic or heterocyclic ring;

U is selected from the group consisting of sulfur, oxygen, $NR^{12}$, CO, SO, $SO_2$, $CO_2$, $NR^{13}CO_2$, $NR^{14}CONR^{15}$, $NR^{16}SO_2$, $NR^{17}SO_2NR^{18}$, $SO_2NR^{19}$, $NR^{20}CO$, $CONR^{21}$, $PO_2R^{22}$ and $PO_3R^{23}$ or U is absent;

$R^1$, $R^2$ and $R^{11}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

$R^8$ is selected from the group consisting of hydrogen, alkyl, substituted alkyl, alkenyl, substituted alkenyl, alkynyl, substituted alkynyl, aralkyl, cycloalkyl, aryl, substituted aryl, heterocyclo excluding imidazole or substituted heterocyclo excluding imidazole;

R, S and T are selected from the group consisting of $CH_2$, CO and $CH(CH_2)_pQ$ wherein Q is $NR^{24}R^{25}$ or $OR^{26}$;

and A, B, C and D are carbon, oxygen, sulfur or nitrogen, except that one of A, B, C, or D is absent to allow the formation of a 5-membered ring;

with the proviso that $R^{11}$ may be hydrogen except when U is SO, $SO_2$, $NR^{13}CO_2$ or $NR^{16}SO_2$.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl' refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by hydroxy, alkyl, alkoxy, aryl, substituted aryl, substituted alkyl or aralkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term 'alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to a optionally substituted, saturated cyclic hydrocarbon ring systems, preferably containing 1 to 3 rings and 3 to 7 carbons per ring which may be further fused with an unsaturated C3-C7 carbocyclic ring.

Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms heterocyclic and "heterocycle" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl) or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocycles, such as, epoxides and aziridines.

The term "heteroatoms" shall include oxygen, sulfur and nitrogen.

The 'ABCD' fused ring to the diazepine ring may be monocyclic or bicyclic, e.g. naphthyl or quinolyl in nature.

The compounds of formula I may form salts which are also within the scope of this invention. Pharmaceutically acceptable (i.e. non-toxic, physiologically acceptable) salts are preferred, although other salts are also useful, e.g, in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compounds I–II with the desired ion in a medium in which the salt precipitates or in an aqueous medium followed by evaporation. Other salts can be formed as known to those skilled in the art.

The compounds of formula I may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compounds I–II in an equivalent amount of the acid in a medium in which the salt precipitates or in an aqueous medium followed by evaporation.

In addition, zwitterions ("inner salts") may be formed.

Compounds of the formula I may also have prodrug forms. Any compound that will be converted in vivo to provide the bioactive agent (i.e., the compound for formula I) is a prodrug within the scope and spirit of the invention.

For example compounds of the formula I may be a carboxylate ester moiety. The carboxylate ester may be conveniently formed by esterifying any of the carboxylic acid functionalities found on the disclosed ring structure(s).

Various forms of prodrugs are well known in the art. For examples of such prodrug derivatives, see:
a) *Design of Prodrugs*, edited by H. Bundgaard, (Elsevier, 1985) and *Methods in Enzymology*, Vol. 42, p. 309–396, edited by K. Widder, et al. (Academic Press, 1985);
b) *A Textbook of Drug Design and Development*, edited by Krosgaard-Larsen and H. Bundgaard, Chapter 5, "Design and Application of Prodrugs," by H. Bundgaard, p. 113–191 (1991);
c) H. Bundgaard, *Advanced Drug Delivery Reviews*, 8, 1–38 (1992);
d) H. Bundgaard, et al., *Journal of Pharmaceutical Sciences*, 77, 285 (1988); and
e) N. Kakeya, et al., *Chem Phar Bull*, 32, 692 (1984).

It should further be understood that solvates (e.g., hydrates) of the compounds of formula I are also within the scope of the present invention. Methods of solvation are generally known in the art.

Preferred Moieties

For compounds of the present invention, the following moieties are preferred:

Compounds of formula I wherein "ABCD" and 'ABC" are a carbocyclic ring.

More preferred are compounds of formula I wherein "ABCD' is a carbocyclic ring, e.g. benzo.

Use and Utility

The compounds of formula I are inhibitors of S-farnesyl protein transferase. They are thus useful in the treatment of a variety of cancers, including (but not limited to) the following;

carcinoma, including that of the bladder, breast, colon, kidney, liver, lung, including small cell lung cancer, ovary, prostate, testes, pancreas, esophagus, stomach, gall bladder, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma;

hematopoietic tumors of myeloid lineage, including acute and chronic myelogenous leukemias, myelodysplastic syndrome and promyelocytic leukemia;

tumors of the central and peripheral nervous system, including astrocytoma, neuroblastoma, glioma, and schwannomas;

tumors of mesenchymal origin, including fibrosarcoma, rhabdomyoscarcoma, and osteosarcoma;

other tumors, including melanoma, xenoderma pigmentosum, keratoactanthoma, seminoma, thyroid follicular cancer and teratocarcinoma.

The compounds of formula I are especially useful in treatment of tumors having a high incidence of ras involvement, such as colon, lung, and pancreatic tumors and in tumors in which a prenyl transferase contributes to tumor maintenance, tumor growth or tumor development. By the administration of a composition having one (or a combination) of the compounds of this invention, development of tumors in a mammalian host is reduced, or tumor burden is reduced, or tumor regression is produced.

Compounds of formula I may also inhibit tumor angiogenesis, thereby affecting the growth of tumors. Such anti-angiogenesis properties of the compounds of formula I may also be useful in the treatment of certain forms of blindness related to retinal vascularization.

Compounds of formula I may also be useful in the treatment of diseases other than cancer that may be associated with signal transduction pathways operating through ras, e.g., neurofibromatosis, atherosclerosis, pulmonary fibrosis, arthritis, psoriasis, glomerulonephritis, restenosis following angioplasty or vascular surgery, hypertrophic scar formation, polycystic kidney disease and endotoxic shock. Compounds of formula I may be useful as anti-fungal agents.

Compounds of formula I may induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpes virus, pox virus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

Compounds of formula I may also be useful in the treatment of diseases associated with farnesyl transferase substrates other than ras (e.g., nuclear lamins, transducin, rhodopsin kinase, cGMP phosphodiesterase, TC21, phosphorylase kinase, Rap2, RhoB, RhoE, PRL1) that are also post-translationally modified by the enzyme farnesyl protein transferase.

Compounds of formula I may also act as inhibitors of other prenyl transferases (e.g., geranylgeranyl transferase I and II), and thus be effective in the treatment of diseases associated with other prenyl modifications (e.g., geranylgeranylation) of proteins (e.g. the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glen, et al., *Science*, 256, 1331 (1992)].

The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate. Suitable cytotoxic agents which may be used in combination with the compounds of the present invention include the taxanes, e.g. paclitaxel, docetaxel or derivatives thereof; camptothecin derivatives e.g. topotecon or CPT-11; gemcitabine; platinum compounds e.g. cisplatin or carboplatin; telomerase inhibitors; various alkylating agents and tubulin stabilizing agents, e.g. epothilones among others.

Farnesyl transferase assays were performed as described in V. Manne et al., Drug Development Research, 34, 121–137, (1995). The compounds of Examples 1–50 inhibited farnesyl transferase with IC50 values between 0.1 nM and 100 $\mu$M.

The compounds of this invention may be formulated with a pharmaceutical vehicle or diluent for oral, intravenous, intraperitoneal, subcutaneous, intraabdominal, intramuscular, rectal, vaginal or topical administration. Oral administration may involve the use of slow release formulations, such as biodegradable polymers or prodrugs. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 400 mg/kg/day, in a single dose or in 2 to 4 divided doses.

Process of Preparation

Compounds of Formula I are prepared by the following schemes.

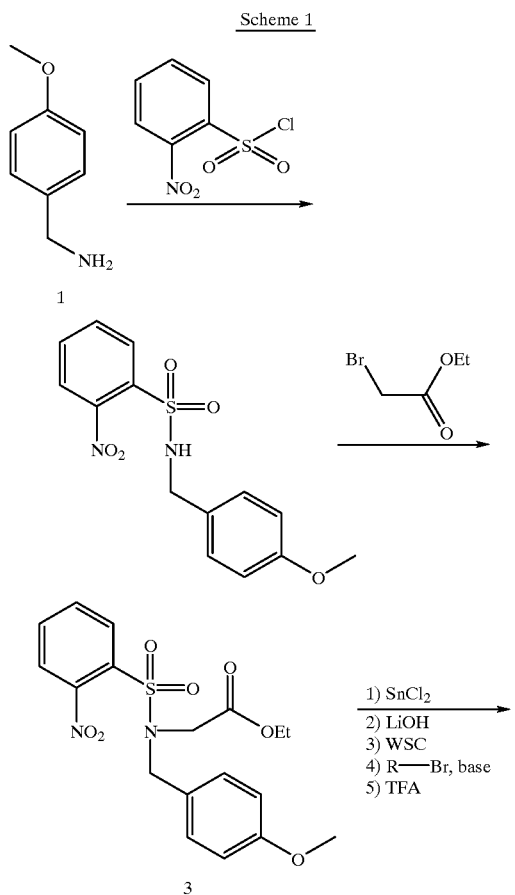

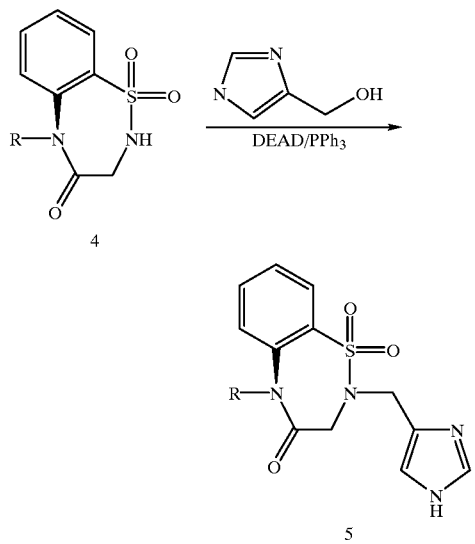

Step 1

In Scheme 1, a compound 1 is coupled to an o-nitrophenylsulfonyl chloride to give a compound 2 using a base such as potassium carbonate in a solvent such as methylene chloride at between zero degrees and room temperature to give a compound 2.

Step 2

A compound 2 is further reacted with bromoethyl acetate in DMF using a base such as potassium carbonate to give a compound 3.

Step 3

A compound 3 is reduced using a reducing agent such as tin chloride in a solvent such as ethyl acetate. Following filtration and concentration, the residue is treated with a base such as lithium hydroxide in a solvent mixture such as THF/methanol/water at room temperature. Following the usual workup, the residue is treated with an alkyl or aryl bromide in a solvent such as DMF using a base such as potassium carbonate. Following the usual workup, the residue is treated with TFA to give a Compound 4.

Step 4

A compound 4 is treated with 4-imidazole methanol in a solvent such as THF under typical Mitsunobu conditions using reagents such as diisopropylazodicarboxylate and triphenylphosphine at room temperature. Standard workup and chromatography give a compound 5.

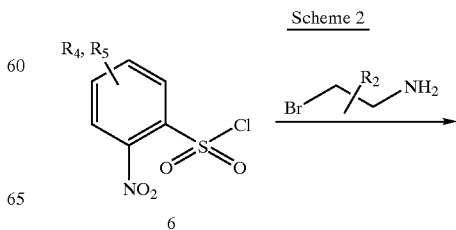

9

-continued

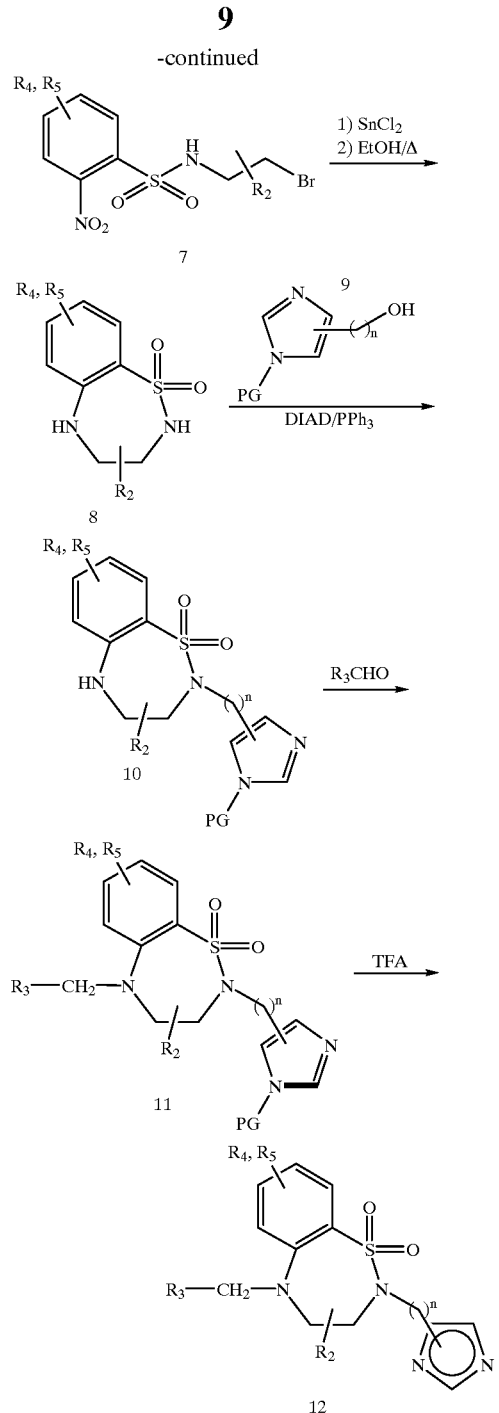

Step 1
In Scheme 2, a Compound 6 is alkylated with 2-bromoethylamine using a solvent such as THF at room temperature to give a compound 7.

Step 2
A compound 7 is reduced using a reducing agent such as tin chloride in a solvent such as ethyl acetate. On workup, the residue is cyclized using a solvent such as ethanol and heating to a temperature such as 80° C. to give a compound 8.

Step 3
The compound 9 is coupled to 8 by using diisopropylazodicarboxylate and resin-bound triphenylphosphine in an organic solvent such as THF at 50° C. to give a compound 10.

10

Step 4
Thereafter, the various products can undergo reductive alkylation in the presence of an acid e.g. dichloroethane at about room temperature to 60° C. Reductive alkylation may also be performed using hydrogen and a catalyst such as Pd on carbon in a solvent such as ethanol in the presence of an acid such as acetic acid at about room temperature.

Step 5
The imidazole protecting group is removed, for example, trityl by an acid such as TFA in an organic solvent such as methylene chloride.

The invention will now be further described by the following examples, which are preferred embodiments of the invention. All temperatures are in degrees Celsius (° C.) unless otherwise indicated. These examples are illustrative rather than limiting.

EXAMPLES

Example 1

2,3-Dihydro-2-(1H-imidazol-4-ylmethyl)-5-(2-phenylethyl)-1,2,5-benzothiadiazepin-4(5H)-one 1, 1-dioxide

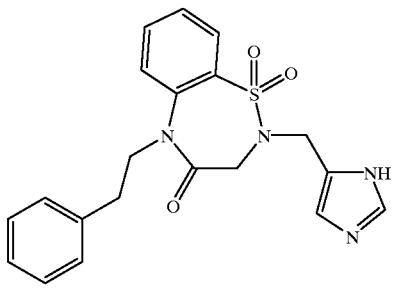

A. N-p-Methoxybenzyl-2-nitrobenzenesulfonamide
To a stirred suspension of p-methoxybenzylamine (7.0 g, 51 mmol) in $CH_2Cl_2$ and saturated $K_2CO_3$ was added 2-nitrobenzenesulfonyl chloride (11.0 g, 50 mmol) at 0° C. The mixture was allowed to stir at 0° C. for 2 h, and partitioned between CH2Cl2 and water. The organic layer was separated, and dried, concentrated in vacuo to give a solid (18 g, 100%).

B. Ethyl N-p-Methoxybenzyl-2-nitrobenzenesulfonamido N-acetate
To a stirred solution of the compound A (18 g, 50 mmol) in DMF in the presence of $K_2CO_3$, was added ethyl bromoacetate (9.0 g). The mixture was allowed to stir at room temperature under argon for 18 h. The mixture was partitioned between ether and water, the organic layer was dried over ($MgSO_4$), filtered and concentrated to an oil (20 g, 100%).

C. Ethyl N-p-Methoxybenzyl-2-aminobenzenesulfonamido N-acetate
To a stirred solution of the compound B (25.0 g, mmol) in ethyl acetate (500 mL) was added $SnCl_2 \cdot 2H_2O$. The solution was allowed to stir at room temperature for 18 h. Saturated $K_2CO_3$ was added, followed by solid $K_2CO_3$. The mixture was filtered, the filtrate was concentrated in vacuo to give an oil (19 g, 100%)

D. N-p-Methoxybenzyl-2-aminobenzenesulfonamido N-acetic Acid
To a stirred solution of compound C (19 g, 50 mmol ) in $THF/MeOH/H2O$ was added $LiOH \cdot H_2O$. The mixture was allowed to stir for 2 h, and adjusted to pH 1.0 with 5% HCl.

The solvent was removed, residue was partitioned between ethyl acetate and water. The organic layer was separated, dried, concentrated to give an oil (17 g, 95%).

E. 2,3-Dihydro-2-[(4-methoxyphenyl)methyl]-1,2,5-benzothiadiazepin-4(5H)-one 1,1-dioxide To a stirred solution of the compound D in acetonitrile at room temperature was added WSC. The mixture was allowed to stir at room temperature for 2 h. The solvent was removed in vacuo, residue was partitioned between ethyl acetate and 10% HCl. The organic layer was dried, concentrated in vacuo and the residue was crystallized from methanol to give a solid (10 g, 60%).

F. 2,3-Dihydro-2-[(4-methoxyphenyl)methyl]-5-(2-phenylethyl)-1,2,5-benzothiadiazepin-4(5H)-one 1,1-dioxide To a stirred solution of the compound E (170 mg, 0.51 mmol) in DMF in the presence of $K_2CO_3$ and cat. amount of 18-c-6 was added the phenethyl bromide (150 uL). The mixture was allowed to stir for 18 h, and partitioned between ether and water. The organic layer was separated, dried, concentrated and residue was purified by silica gel chromatography (2:1, hexanes/ethyl acetate) to give an oil (100 mg, 46%).

G. 2,3-Dihydro-5-(2-phenylethyl)-1,2,5-benzothiadiazepin-4(5H)-one 1,1-dioxide

To a stirred solution of the compound F (100 mg. 0.23 mmol) in $CH_2Cl_2$ in the presence of anisole (100 uL, 0.93 mmol) at 0° C. was added trifluoromethanesulfonic acid (40 uL). The mixture was partitioned between ethyl acetate and sat'd NaHCO3 solution. The organic layer was separated, dried, concentrated in vacuo. The residue was purified by chromatography (1:1, hexanes/ethyl acetate) to give an oil (60 mg, 83%).

H. 2,3-Dihydro-5-(2-phenylethyl)-2-[[1-(triphenylmethyl)-1H-imidazol-4-yl]methyl]-1,2,5-benzothiadiazepin-4(5H)-one 1,1-dioxide To a stirred suspension of the compound G (100 mg, 0.32 mmol) and tritylimidazolemethanol (150 mg, 0.44 mmol) in the presence of triphenylphosphine (120 mg, 0.44 mmol) at 80° C. was added DEAD (70 uL, 0.44 mmol). The solution was allowed to stir for 30 min, then the solvent was removed, the residue was purified by chromatography to give an oil (150 mg, 70%). MS (M+H) 639.

I. 2,3-Dihydro-2-(1H-imidazol-4-ylmethyl)-5-(2-phenylethyl)-1,2,5-benzothiadiazepin-4(5H)-one, 1,1-dioxide To a stirred solution of the compound H (150 mg, 0.23 mmol) in DCE, was added TFA (1 mL), and $Et_3SiH$ (0.5 mL). The mixture was allowed to stir for 30 min, and partitioned between ethyl acetate and sat'd $NaHCO_3$ solution. The organic layer was separated, dried, concentrated, the residue was purified by chromatography (10:1, ethyl acetate and methanol) to give an oil. This was dissolved in methanol, 1N HCl solution in ether was added, the solvent was removed to give a solid (90 mg, 98%). MS (M+H) 397.

Example 2

2,3-Dihydro-2-[(1-methyl-1H-imidazol-5-yl)methyl]-5-(2-phenylethyl)-1,2,5-benzothiadiazepin-4(5H)-one 1,1-dioxide

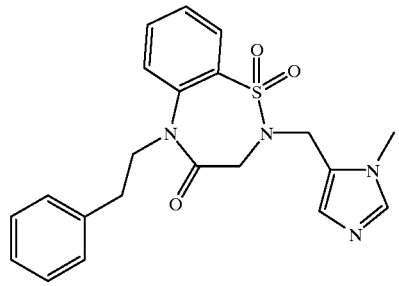

To a stirred solution of the compound H (45 mg, 0.07 mmol) of Example 1 in DCE at 0° C. under argon, was added methyl triflate. The mixture was allowed to stir for 15 min, then TFA followed by $Et_3SIH$ was added. The mixture was partitioned between ethyl acetate and sat'd $NaHCO_3$. The organic layer was separated, dried, concentrated. The residue was purified by chromatography (10:1 ethyl acetate/metanol) to give an oil. This was dissolved in methanol, and 1 N HCl in ether was added, solvent was removed to give a solid (14 mg, 50%). MS (M+H) 411.

Example 3

2,3-Dihydro-2-(1H-imidazol-4-ylmethyl)-5-(phenylmethyl)-1,2,5-benzothiadiazepin-4(5H)-one 1,1-dioxide

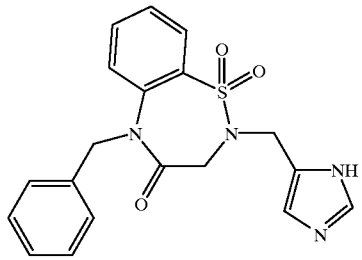

The title compound was prepared by employing the method described for the preparation of Example 1 from compound E of the Example 1, except benzyl bromide was used in the place of phenethyl bromide. MS (M+H) 383.

Example 4

(S)-3,4-Dihydro-2-(1H-imidazol-4-ylmethyl)-4-oxo-β-phenyl-1,2,5-benzothiadiazepine-5(2H)-acetic acid methyl ester 1,1-dioxide

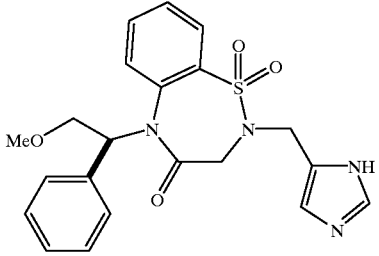

The title compound was prepared by employing the method described for the preparation of Example 1 from the compound E of the Example 1, except methyl alphabromophenyl acetate was used in the place of phenethyl bromide. MS (M+H) 441.

Example 5

(S)-3,4-Dihydro-2-(1H-imidazol-4-ylmethyl)-β-phenyl-1,2,5-benzothiadiazepine-5(2H)-ethanol 1,1-dioxide

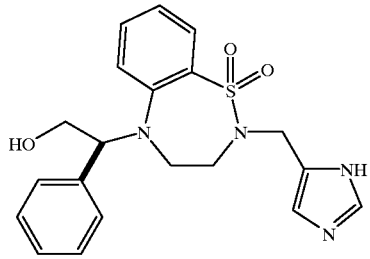

To a stirred solution of Example 4 (117 mg, 0.17 mmol) in diglyme (5 mL) was added diborane (2.55 mL, 1M in THF). The mixture was stirred at room temperature for 18 hours, with addition of more diborane (3 mL, 1M in THF) and subsequent stirring at 75° C. for 48 hours. The mixture was cooled to room temperature, diluted with ethyl acetate (20 mL), and ammonium hydroxide (3 mL) and stirred for 15 min. The solution was poured into aqueous sodium hydroxide (50 mL, 1N), extracted with ethyl acetate (3×50 mL), dried (MgSO4) and concentrated in vacuum to a crude oil. The oil was purified using preparative HPLC (aqueous methanol gradient containing 0.1% trifluoroacetic acid eluted on an ODS 5×25 cm column) and lyphilized from water to provide the title compound (20 mg, 30%) as white solid.

MS (M+H) 399.

Example 6

2,3,4,5-Tetrahydro-2-(1H-imidazol-4-ylmethyl)-5-(phenylmethyl)-1,2,5-benzothiadiazepine 1,1-dioxide

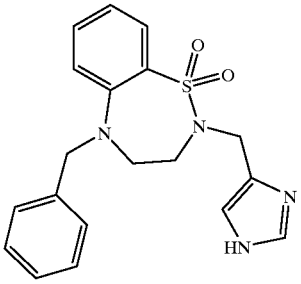

A. N-(2-Bromoethyl)-2-nitrobenzenesulfonamide

To a stirred solution at 0° C. of 2-nitrobenzenesulfonyl chloride (2.2 g, 10 mmol) in methylene chloride (50 mL) and aqueous NaHCO₃ solution (50 mL) was added bromoethylamine hydrobromide (4.1 g, 20 mmol). The mixture was stirred at 0° C. for 3 hours. The organic layer was separated and washed with 10% HCl solution and saturated NaHCO₃ solution, dried and concentrated to give Compound A as an oil (3.0 g, 97%).

B. 2,3,4,5-Tetrahydro-1,2,5-benzothiadiazepine 1,1-dioxide

To a stirred solution of Compound A (3 g, 9.7 mmol) in ethyl acetate (100 mL) was added solid tin chloride dihydrate (SnCl₂·2H₂O, 7 g, 31.2 mmol). The mixture was stirred for 18 hours. A saturated solution of K₂CO₃ (4 mL) was added, followed by solid K₂CO₃ (10 g). The suspension was stirred for 3 hours and filtered. The filtrate was concentrated under vacuum to give N-2-bromoethyl-2'-aminobenzenesulfonamide, which is dissolved in ethanol (50 mg). This alcoholic solution was heated at reflux for 3 days. The solution was cooled and concentrated under vacuum to give Compound B as a solid (1.5 g, 78%).

C. 1-(Triphenylmethyl)-1H-imidazole-4-methanol

Diisopropylethylamine (14 mL, 80 mmol) was added dropwise to a suspension of 4-imidazole methanol (5.4 g, 40 mmol) in CH₃CN (15 mL) at 0° C. A homogeneous yellow solution was formed. To this solution was added triphenylmethyl chloride (11.2 g, 40 mmol). The reaction mixture was stirred at room temperature for 2 h. The resultant white precipitate was filtered and washed successively with saturated NaHCO₃ aqueous solution (2×20 mL) and water (2×20 mL), then dried in a vacuum oven (45° C.) for 12 h to afford a white solid 11.2 g (82%) which was used in next step without further purification.

D. 2,3,4,5-Tetrahydro-2-[[1-(triphenylmethyl)-1H-imidazol-4-yl]methyl]-1,2,5-benzothiadiazepine 1,1-dioxide To a suspension of Compound C (200 mg, 1 mmol), Compound B (340 mg, 1 mmol) and polymer-supported triphenylphosphine (1 g, 3 mmol) was added dropwise DIAD (0.2 mL, 1 mmol) in THF (10 mL). The mixture was stirred at 50° C. for 3 h. The polymeric material was filtered off and was thoroughly washed with CH₂Cl₂ (3×10 mL). The filtrate was successively washed with 1 M NaOH (20 mL) and brine (20 mL), then dried (Na₂SO₄) and evaporated under reduced pressure to afford 521 mg as a sticky solid, which was used in next step without further purification.

LC-MS: (M+H)⁺ 521.

E. 2,3,4,5-Tetrahydro-5-(phenylmethyl)-2-[[1-(triphenylmethyl)-1H-imidazol-4-yl]methyl]-1,2,5-benzothiadiazepine 1,1-dioxide To a solution of compound D (130 mg, 0.25 mmol) in 1,2-DCE (10 mL) was successively added benzaldehyde (0.3 mL, 3 mmol) and HOAc (0.5 mL). After stirring at room temperature for 0.5 h, NaBH(OAc)$_3$ (212 mg, 1 mmol) was added and the reaction mixture was stirred at 50° C. for 2 h. An additional portion of NaBH(OAc)$_3$ (212 mg, 1 mmol) was added. The reaction mixture was stirred at 50° C. for 12 h, and was then cooled to room temperature, neutralized with NH$_4$OH to pH 9, diluted with CH$_2$Cl$_2$ (50 mL) and water (50 mL). The layers were separated and the organic phase was washed with water (2×30 mL), dried (Na$_2$SO$_4$) and evaporated under reduced pressure to provide a solid residue.

To a solution of the above residue in CH$_2$Cl$_2$ (10 mL) was dropwise added TFA (4 mL) at 0° C. The reaction mixture was stirred at room temperature for 2 h and evaporated under reduced pressure. The residue was purified by preparative HPLC (YMC S-15 ODS column, 30×250 mm; solvent A, 0.1% TFA in 90% water and 10% methanol; solvent B, 0.1% TFA in 10% water and 90% methanol: 35–100% B in 30 min, flow rate 25 mL/min; UV monitored at 220 nm). Fractions containing the desired product were combined, neutralized with saturated Na$_2$CO$_3$ aqueous solution, then extracted with CH$_2$Cl$_2$. The combined extracts were dried (Na$_2$SO$_4$) and evaporated under reduced pressure. The residue was redissolved in MeOH (15 mL) and 1N HCl solution in ether (5 mL) was added. The solvent was removed in vacuo to give 16 mg (HCl salt) as a yellow solid, purity >97% (YMS S-3 ODS column, 0.46×50 mm, 220 nm, 1.5 mL/min, 0–100% B in A over 8 minutes (solvent A, 0.2% H$_3$PO$_4$ in 90% water and 10% methanol; solvent B, 0.2% H$_3$PO$_4$ in 10% water and 90% methanol, RT 5.6 min, HI>97%).

LC-MS (M+H)$^+$ 369.

Example 7

2,3,4,5-Tetrahydro-2-(1H-imidazol-4-ylmethyl)-5-(2-phenylethyl)-1,2,5-benzothiadiazepine 1,1-dioxide

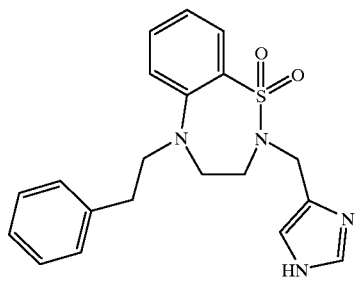

A. 2,3,4,5-Tetrahydro-5-(2-phenylethyl)-2-[[1-(triphenylmethyl)-1H-imidazol-4-yl]methyl]-1,2,5-benzothiadiazepine 1,1-dioxide Compound A was prepared starting from compound D of Example 6 and phenylacetaldehyde (0.18 mL, 1.5 mmol) using the procedure outlined in Example 6E to yield 40 mg of the compound.

LC-MS (M+H)$^+$ 383.

Example 8

2,3,4,5-Tetrahydro-2-(1H-imidazol-4-ylmethyl)-5-[(2-methoxyphenyl)methyl]-1,2,5-benzothiadiazepine 1,1-dioxide

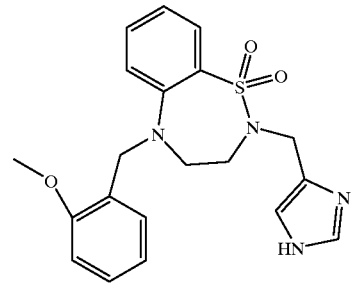

A. Compound A was prepared starting from compound D of Example 6 and o-methoxy benzaldehyde using the procedure outlined for compound E of Example 6 to yield 30 mg. LC-MS (M+H)$^+$399.

Example 9

8-Bromo-2,3,4,5-tetrahydro-2-(1H-imidazol-4-ylmethyl)-5-(phenylmethyl)-1,2,5-benzothiadiazepine 1,1-dioxide

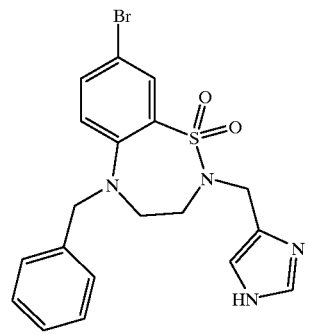

A. 8-Bromo-2,3,4,5-tetrahydro-1,2,5-benzothiadiazepine 1,1-dioxide

To a suspension of compound B of Example 6 (500 mg, 2.5 mmol) in CH$_2$Cl$_2$ (6 mL) was added a solution of tetrabutylammonium tribromide (1.3 g, 2.7 mmol) in CH$_2$Cl$_2$ (2 mL). The reaction mixture was stirred at room temperature for 40 min and was then diluted with CH$_2$Cl$_2$ (50 mL). The reaction mixture was washed successively with saturated aqueous NaHCO$_3$ (20 mL), brine (20 mL), then dried (Na$_2$SO$_4$) and evaporated under reduced pressure to afford a green oil, purification by flash column chromatography (CHCl$_3$/MeOH=95/5) and concentration of the appropriate fractions afforded a gray solid. This was used in the next step without further purification.

LC-MS: (M+H)$^+$=279.

B. 8-Bromo-2,3,4,5-tetrahydro-2-[[1-(triphenylmethyl)-1H-imidazol-4-yl]methyl]-1,2,5-benzothiadiazepine 1,1-dioxide Compound B was prepared from Compound A as described for Compound D of Example 6, and was used in the next step without further purification.

C. 8-Bromo-2,3,4,5-tetrahydro-2-(1H-imidazol-4-ylmethyl)-5-(phenylmethyl)-1,2,5-benzothiadiazepine 1,1-dioxide Compound C was prepared from Compound B as described for Compound E of Example 6 to give 24 mg of Compound C.

LC-MS (M+H)+ 448.

Example 10

2,3,4,5-Tetrahydro-2-(1H-imidazol-4-ylmethyl)-5-[(3-methoxyphenyl)methyl]-1,2,5-benzothiadiazepine 1,1-dioxide

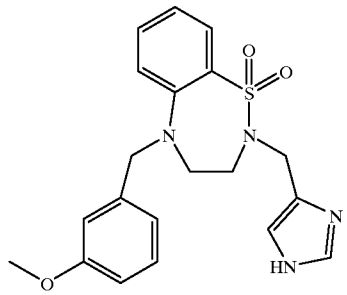

A. Compound A was prepared starting from Compound D of Example 6 and m-methoxy benzaldehyde using the procedure outlined for Compound E of Example 6. Yield-57 mg.

LC-MS (M+H)+ 399.

Example 11

2,3,4,5-Tetrahydro-2-(1H-imidazol-4-ylmethyl)-1,2,5-benzothiadiazepine 1,1-dioxide

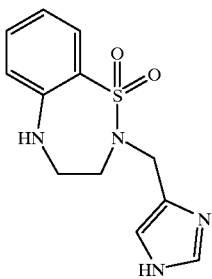

Preparation of A:

To a solution of Compound D of Example 6 (57 mg, 0.11 mmol) in CH₂Cl₂ (8 mL) at 0° C. was successively added a solution of 20% TFA in CH₂Cl₂ (10 mL) and triethylsilane (0.017 mL, 0.11 mmol). The reaction mixture was stirred at room temperature for 2 h. The solvent was removed under reduced pressure. The residue was triturated with hexanes (3×10 mL) and purified by preparative HPLC (YMC S-15 ODS column, 30×250 mm; solvent A, 0.1% TFA in 90% water and 10% methanol; solvent B, 0.1% TFA in 10% water and 90% methanol: 30–100% B in 30 min, flow rate 25 mL/min; UV monitored at 220 nm). Fractions containing the desired product were combined, neutralized with saturated aqueous NaHCO₃, then extracted with CH₂Cl₂. The combined extracts were dried (Na₂SO₄) and evaporated under reduced pressure. The residue was redissolved in MeOH (10 mL) and 1N HCl solution in ether (5 mL) was added. The solvent was removed in vacuo to give 20 mg (63%) of Compound A (HCl salt) as a yellow solid.

LC-MS (M+H)+ 279.

Example 12

2,3,4,5-Tetrahydro-2-[2-(1H-imidazol-2-yl)ethyl]-5-(phenylmethyl)-1,2,5-benzothiadiazepine 1,1-dioxide

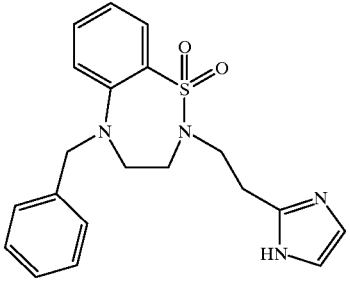

A. 1-(Triphenylmethyl)-1H-imidazole

To a solution of imidazole (6.8 g, 0.1 mol) in dimethylformamide (100 mL) was added triethylamine (33.5 mL, 0.24 mol) and a solution of trityl chloride (30.7 g, 0.11 mol) in dimethylformamide (200 mL). The mixture stirred for 16 hr under nitrogen followed by addition to water (500 mL). A white precipitate formed and was filtered, washed with ethyl acetate and dried to yield 33 g (99%) of Compound A as a white powder. (M+Na)+ 333.

B. 1-(Triphenylmethyl)-1H-imidazole-2-ethanol

To a cooled (0° C.) solution of Compound A (15.5 g, 50 mmol) in THF was added nBuLi (34.4 mL, 55 mmol) dropwise over 30 minutes. The mixture was stirred for 1 h followed by gentle warming to 30° C. over 30 minutes. The solution was cooled to 0° C. and ethylene oxide (24.4 mL, 50 mmol) was added to the reaction mixture via a cannula. The mixture stirred at 0° C. for 2 hr and was gradually warmed to ambient temperature over 16 hr. The solution was concentrated and chromatographed (flash silica 7.0×15 cm, 19:1; C:M) to yield 14.5 g (82%) of Compound B as a white solid.

MS (M+Na)+ 377.

C. 2,3,4,5-Tetrahydro-2-[2-(1H-imidazol-2-yl)ethyl]-1,2,5-benzothiadiazepine 1,1-dioxide Compound C was prepared from Compound B of Example 6 using the procedures outlined for the preparation of Compounds D and E of Example 6.

LC-MS (M+H)+ 383.

Example 13

2,3,4,5-Tetrahydro-2-[2-(1H-imidazol-4-yl)ethyl]-5-(phenylmethyl)-1,2,5-benzothiadiazepine 1,1-dioxide

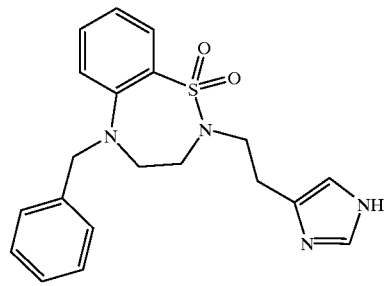

A. 1H-imidazole-4-ethanoic acid ethyl ester

To a suspension of 4-imidazole ethanoic acid (8.8 g, 0.054 mol) in EtOH (50 mL) at 0° C. was added thionyl chloride (3.6 mL, 0.054 mol). The reaction mixture was stirred at room temperature for 12 h. Solvent was removed under reduced pressure to provide of 9.8 g (95%) of a blue solid, which was used in next step without further purification.

LC-MS: (M+H)$^+$ 155.

B. 1-(Triphenylmethyl)-1H-imidazole-4-ethanoic acid ethyl ester

Diisopropylethylamine (14 mL, 80 mmol) was added dropwise to a suspension of Compound A (5.4 g, 40 mmol) in CH$_3$CN (15 mL) at 0° C. A homogeneous yellow solution was formed. To this solution was added triphenylmethyl chloride (11.2 g, 40 mmol). The reaction mixture was stirred at room temperature for 2 h. The resultant white precipitate was filtered and washed successively with saturated NaHCO$_3$ aqueous solution (2×20 mL) and water (2×20 mL), then dried in a vacuum oven (45° C.) for 12 h to afford a white solid 11.2 g (82%) which was used in the next step without further purification.

C. 1-(Triphenylmethyl)-1H-imidazole-4-ethanol

To a suspension of compound B (18 g, 0.045 mol) in THF (60 mL) at 0° C. was added a solution of LAH in THF (100 mL, 0.10 mol) through an addition funnel. The solution was stirred at room temperature for 12 h. The reaction mixture was then cooled to 0° C. and MeOH (50 mL) was added dropwise. Solvent was removed under reduced pressure. The residue was dissolved in THF (150 mL) and basified with 1M NaOH (100 mL). The mixture was extracted with CH$_2$Cl$_2$ (3×100 mL). The combined extracts were dried (Na$_2$SO$_4$) and evaporated under reduced pressure. The residue was purified by flash column chromatography (2% MeOH in CHCl$_3$) to provide 6 g (38%) of a white solid.

D. 2,3,4,5-Tetrahydro-2-[3-(1H-imidazol-4-yl)ethyl]-5-(phenylmethyl)-1,2,5-benzothiadiazepine 1,1-dioxide Compound D was prepared from Compound C and Compound B of Example 13 using the procedures outlined for the preparation of Compounds D and E of Example 6.

LC-MS (M+H)$^+$ 383.

What is claimed is:

1. A compound of the formula $$\text{(I)}$$

or its enantiomer, diasteromer, or its pharmaceutically acceptable salt, prodrug of solvate thereof wherein:

r, s and t are 0 or 1;

p is 0, 1 or 2;

$X^1$ and $X^2$ are each independently selected from the group consisting of hydrogen, alkyl, substituted alkyl, akenyl, substituted alkenyl, alkynyl, substituted alkynyl, aralkyl, cycloalkyl, aryl, substituted aryl, heterocyclo, substituted heterocyclo or when $X^1$ and $X^2$ are taken together they represent an oxygen atom double bonded to the carbon atom of the ring;

Y is selected from the group consisting of CHR$^9$, or CR$^9$R$^{10}$;

Z is —CO—, —SO$_2$— or Z is absent;

R$^6$, R$^7$, R$^9$, R$^{10}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$ and R$^{26}$, are selected from the group consisting of hydrogen, lower alkyl or substituted alkyl;

R$^4$, R$^5$ are selected from the group consisting of hydrogen, halo, nitro, cyano and U-R$^{11}$; R$^4$ and R$^5$ may join together to form a carbocyclic or heterocyclic ring;

U is selected from the group consisting of sulfur, oxygen, NR$^{12}$, CO, SO, SO$_2$, CO$_2$, NR$^{13}$CO$_2$, NR$^{14}$CONR$^{15}$, NR$^{16}$SO$_2$, NR$^{17}$SO$_2$NR$^{18}$, SO$_2$NR$^{19}$, NR$^{20}$CO, CONR$^{21}$, PO$_2$R$^{22}$ and PO$_3$R$^{23}$ or U is absent;

R$^1$, R$^2$ and R$^{11}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

R$^8$ is selected from the group consisting of hydrogen, alkyl, substituted alkyl, alkenyl, substituted alkenyl, alkynyl, substituted alkynyl, aralkyl, cycloalkyl, aryl, substituted aryl, heterocyclo excluding imidazole or substituted heterocyclo excluding imidazole;

R, S and T are selected from the group consisting of CH$_2$, CO and CH(CH$_2$)$_p$Q wherein Q is NR$^{24}$R$^{25}$ or OR$^{26}$;

and A, B, C and D are carbon, oxygen, sulfur or nitrogen;

with the proviso that R$^{11}$ may be hydrogen except when U is SO, SO$_2$, NR$^{13}$CO$_2$ or NR$^{16}$SO$_2$.

2. The compound of claim 1, wherein ABCD is a carbocyclic ring.

3. The compound of claim 1, selected from the group consisting of 2,3-Dihydro-2-(1H-imidazol-4-ylmethyl)-5-(2-phenylethyl)-1,2,5-benzothiadiazepin-4(5H)-one 1,1-dioxide;

2,3-Dihydro-2-[(1-methyl-1H-imidazol-5-yl)methyl]-5-(2-phenylethyl)-1,2,5-benzothiadiazepin-4(5H)-one 1,1-dioxide;

2,3-Dihydro-2-(1H-imidazol-4-ylmethyl)-5-(phenylmethyl)-1,2,5-benzothiadiazepin-4(5H)-one 1,1-dioxide;

(S)-3,4-Dihydro-2-(1H-imidazol-4-ylmethyl)-4-oxo-β-phenyl-1,2,5-benzothiadiazepine-5(2H)-acetic acid methyl ester 1,1-dioxide;

(S)-3,4-Dihydro-2-(1H-imidazol-4-ylmethyl)-β-phenyl-1,2,5-benzothiadiazepine-5(2H)-ethanol 1,1-dioxide;

2,3,4,5-Tetrahydro-2-(1H-imidazol-4-ylmethyl)-5-(phenylmethyl)-1,2,5-benzothiadiazepine 1,1-dioxide;

2,3,4,5-Tetrahydro-2-(1H-imidazol-4-ylmethyl)-5-(2-phenylethyl)-1,2,5-benzothiadiazepine 1,1-dioxide;

2,3,4,5-Tetrahydro-2-(1H-imidazol-4-ylmethyl)-5-[(2-methoxyphenyl)methyl]-1,2,5-benzothiadiazepine 1,1-dioxide;

8-Bromo-2,3,4,5-tetrahydro-2-(1H-imidazol-4-ylmethyl)-5-(phenylmethyl)-1,2,5-benzothiadiazepine 1,1-dioxide;

2,3,4,5-Tetrahydro-2-(1H-imidazol-4-ylmethyl)-5-[(3-methoxyphenyl)methyl]-1,2,5-benzothiadiazepine 1,1-dioxide;

2,3,4,5-Tetrahydro-2-(1H-imidazol-4-ylmethyl)-1,2,5-benzothiadiazepine 1,1-dioxide;

2,3,4,5-Tetrahydro-2-[2-(1H-imidazol-2-yl)ethyl]-5-(phenylmethyl)-1,2,5-benzothiadiazepine 1,1-dioxide; and 2,3,4,5-Tetrahydro-2-[2-(1H-imidazol-4-yl)ethyl]-5-(phenylmethyl)-1,2,5-benzothiadiazepine 1,1-dioxide.

4. A method of inhibiting farnesyl protein transferase which comprises administering to a mammalian subject an effective farnesyl protein transferase inhibiting amount of a compound of claim 1.

5. A method of inhibiting prenyl transferases which comprises administering to a mammalian subject an effective prenyl transferase inhibiting amount of a compound of claim 1.

6. A method of inhibiting tumors which comprises administering to a mammalian subject an effective tumor inhibiting amount of a compound of claim 1.

7. A method of treating diseases associated with signal transduction pathways operating through Ras which comprises administering to a mammalian subject an amount of a compound of claim 1 effective for treating said diseases.

8. A method of treating diseases associated with proteins that are posttranslationally modified by the enzyme farnesyl protein transferase which comprises administering to a mammalian subject an amount of a compound of claim 1 effective for treating said diseases.

9. A method of treating disease associated with proteins that are posttranslationally modified by the enzymes geranylgeranyl protein transferase which comprises administering to a mammalian subject an amount of a compound of claim 1 effective for treating said diseases.

* * * * *